United States Patent [19]
Wyckoff

[11] Patent Number: 5,063,915
[45] Date of Patent: Nov. 12, 1991

[54] MALE GENITAL DEVICE AND METHOD FOR CONTROL OF EJACULATION

[76] Inventor: Robert L. Wyckoff, 2099 W. Lincoln Ave., Napa, Calif. 94558

[21] Appl. No.: 451,940

[22] Filed: Dec. 18, 1989

[51] Int. Cl.$^5$ .......................... A61F 5/00; A61F 6/02
[52] U.S. Cl. ....................................... 128/79; 128/842
[58] Field of Search ................. 128/842, 844, 79, 876, 128/875, 874, DIG. 15; 604/347–353

[56] References Cited

U.S. PATENT DOCUMENTS

| | | | |
|---|---|---|---|
| 1,298,434 | 3/1919 | Baer | 128/79 |
| 1,608,806 | 11/1926 | Nelson | 128/79 |
| 1,615,945 | 2/1927 | James | 128/79 |
| 2,576,024 | 11/1951 | Laser | 128/79 |
| 3,518,995 | 7/1970 | Claff | 128/842 |
| 3,648,700 | 3/1972 | Warner | 604/349 |
| 3,773,040 | 11/1973 | Gavrilovich | 128/79 |
| 3,779,159 | 3/1974 | McIntire | 128/79 |
| 3,799,157 | 3/1974 | McIntire | 128/79 |
| 3,866,611 | 2/1975 | Baumrucker | 128/DIG. 15 |
| 3,893,455 | 7/1975 | McNally | 128/79 |
| 3,970,316 | 7/1976 | Westmoreland | 128/876 |
| 4,149,540 | 4/1979 | Hasslinger | 128/DIG. 15 |
| 4,864,698 | 9/1989 | Brame | 128/DIG. 15 |

OTHER PUBLICATIONS

J. L. McCary, "Human Sexuality—Physiological, Psychological and Sociological Factors," Van Nostrand Rheinhold, New York 1976.
P. Beautrais et al., "Premature Ejaculation—a New Method of Control", Forum Magazine, Forum International Ltd., New York, May 1979.

*Primary Examiner*—Robert A. Hafer
*Assistant Examiner*—Michael Brown
*Attorney, Agent, or Firm*—Armand G. Guibert

[57] ABSTRACT

A method and device by which sexual emission in the male can be delayed or alternatively prevented during sexual activity. The method is based on the physiological fact that a preliminary to ejaculation is a drawing up of the scrotum and an ascent of the testicles. Hence, obstructing such ascent of the testicles delays ejaculation or even prevents it. The device is an annulus-forming member applicable solely around the neck of the scrotum, the annulus formed being of a size barring passage of the testicles so as to obstruct their ascent. The member does not cause pain or discomfort, and does not encumber sexual activity. Further, the annulus formed is easily released and the member removed entirely, if desired, by either party to influence timing of ejaculation readily. The device is useful for treatment of male premature ejaculation as well as treatment, in some cases, of frigidity in the female.

5 Claims, 1 Drawing Sheet

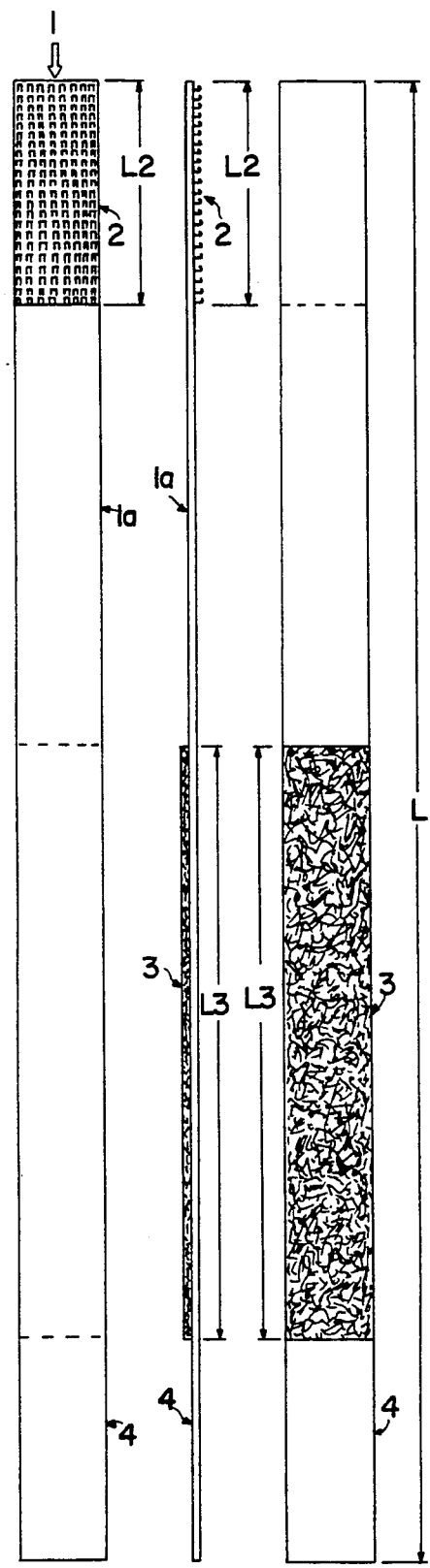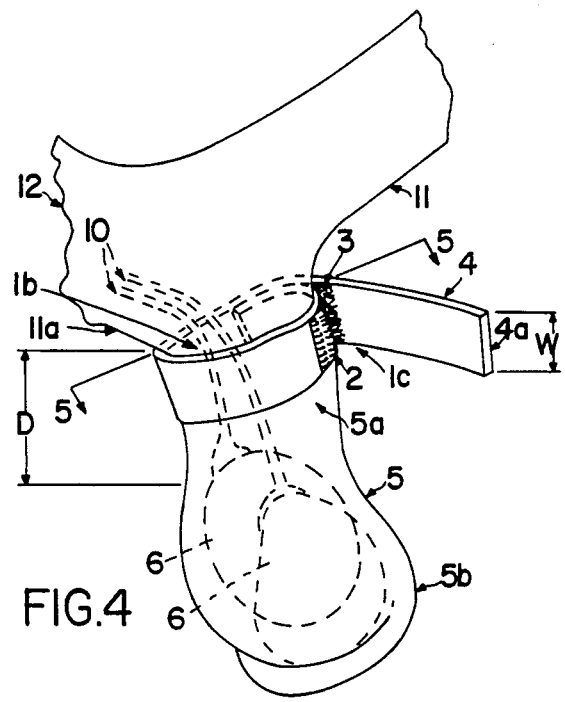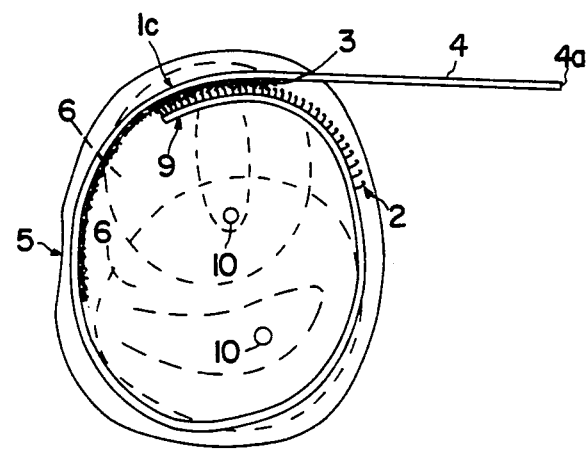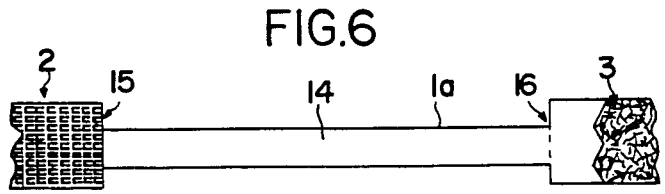

MALE GENITAL DEVICE AND METHOD FOR CONTROL OF EJACULATION

BACKGROUND OF THE INVENTION

Many efforts have been made to control ejaculation to permit prolonged sexual intercourse, or to accommodate a female partner unable to achieve sexual satisfaction as rapidly as the male, or to prevent premature ejaculation. No patent has been found specifically directed to this purpose, though a mechanical method of forcibly holding the male urethra closed at some point in the penis has been tried without much acceptance. Another method of delaying ejaculation has been use of a condom to reduce sensation in the penis but this is frequently unsatisfactory. A chemical method to delay ejaculation relies upon application of a local anesthetic to the glans of the penis or perhaps the entire penis. This treatment is effective in some cases, but at the cost of much-reduced pleasurable sensation. In an article "Premature Ejaculation, a New Method of Control" (Forum Magazine, Forum International Ltd., New York, May 1979), P. Beautrais and A. Colgan have described a manual method of delay requiring the male to pull on his testicles to keep them down and away from their normal ascended position in the scrotum prior to ejaculation. This method involves uncomfortable contortions at an inopportune time. No method is known which gives the female partner any measure of control over the timing of ejaculation during the coitus. Yet, the male's early ejaculation relative to the sexual needs of the female is a rather frequent issue between marital partners and one of the most difficult to treat.

SUMMARY OF THE INVENTION

A principal object of the invention, therefore, is to control male ejaculation in sexual intercourse with minimal interference with the sexual act. One early physiological step in ejaculation is rising of the testicles in the scrotum (see J. L. McCary, "Human Sexuality", Van Nostrand Rheinhold, New York, N.Y., 1976). Thus another object is to delay ejaculation or, in some cases, suppress it by mechanically preventing the rise of the testicles. Yet another object of this invention is to use a device to prevent the rise of the testicles within the scrotum during sexual activity, removing it when ejaculation is desired. As a further object, the device should be of minimal encumbrance, quickly and easily released and removed by the male or female participant when it is desired that the male proceed to ejaculation.

Accordingly, the invention concerns a method and device for delaying or alternatively preventing ejaculation by the generative organ of a male, the organ having a base with a scrotum depending from it, which scrotum has a first portion proximal to the base and a second portion containing testicles normally resting at a particular distance from the base when the scrotum is in an inactive state, the testicles having a maximum combined cross-section of given area; comprising an elongated, inelastic flexible member, the member having a pair of spaced lateral boundaries defining a width corresponding to a substantial fraction of the particular distance; one part of the elongated member, including one end thereof, being formable into an annulus circumscribing the first portion of the scrotum with the pair of boundaries lying solely below the base; the remainder of the elongated member having—adjacent the other end—a tab section of length at least readily graspable between the thumb and a finger of a hand, the tab section remaining external to the annulus; the one part having a manually-operable, adjustable-length fastening thereon for closing the annulus, that annulus when closed having an adjusted circumference encompassing an area non-clamping with respect to the first portion of the scrotum but substantially less than the given area of the combined testicle cross-section to confine thereby the testicles to the second portion of the scrotum during sexual activity of duration otherwise sufficient to initiate ejaculation; and the fastening being releasable in response to a pull on the tab section for opening the annulus after a desired delay; whereby, upon the opening of the annulus by the pull, the entire device is removable to a location remote from the scrotum and the testicles are freed from confinement, ascent of the freed testicles permitting ejaculation.

The invention will now be described in conjunction with the following drawing.

DESCRIPTION OF THE DRAWING

Preferred embodiments of the invention are illustrated in the accompanying drawing in which:

FIG. 1 is a front view of the outer surface of a preferred embodiment of the device in the open state.

FIG. 2 is an edge view of the device of FIG. 1.

FIG. 3 is a reverse view of the device of FIG. 1 showing the inner (scrotum contacting) surface.

FIG. 4 is a semi-pictorial view of the device of FIG. 1 in its closed circumscrotal position with the secured testicles shown in dashed outline.

FIG. 5 is an edge or top view of the device of FIG. 1 in its encircling or closed circumscrotal position, the view being taken in the direction of the arrows at section 5—5 in FIG. 4.

FIG. 6 is a reverse view similar to that in FIG. 3, but showing part of the device of FIG. 1 modified to have a reduced width over a portion between the device's interengageable connection elements.

BEST MODE FOR IMPLEMENTING THE INVENTION

Referring to FIGS. 1-3, a preferred embodiment of a device 1 according to the invention is shown, the device consisting of a flexible band 1a bearing a pair of interengageable connection elements 2,3 for closure of device 1 after a portion thereof is formed into a ring shape 1c (an "annulus" or, more generally, a "loop," as it will be termed hereinafter), as shown in FIGS. 4 and 5. Annulus 1c encircles an upper portion 5a of a scrotum 5 loosely enough (i.e., without any clamping action) to avoid pain or discomfort to the user as well as any tissue damage to scrotum 5 or a spermatic cord 10, yet tightly enough that its opening 1b is sufficiently small to prevent passage of testicles 6 through that opening 1b. Accordingly, the size of opening 1b is determined by the maximum cross-section of testicles 6, as will be evident to those skilled in the art from scrutiny of FIG. 5. That size is not critical as long as testicular confinement is achieved without discomfort for the user. In this respect, it may be mentioned that—as stated by J. L. McCary (at p. 214 of the book cited previously, second paragraph—titled "The Testes")—a vasoconstrictive reaction increases the size of the testes as intercourse progresses, annulus 1c consequently becoming an even more effective barrier.

The method of closure must nonetheless allow for some variation in the size (opening 1b) of annulus 1c to accommodate differences in girth of the scrotal sac (5 in FIGS. 4,5) from time to time and from one man to another. Connection elements or "closure" 2,3 shown in FIGS. 1-5 (as it will be termed hereinafter) is that known under the Trademark "Velcro" in which stiff monofilament fingers bent into a distal hook shape 2 can engage an irregular fiber bed 3 at any desired longitudinal location. When elements 2,3 are pressed together, engagement of the Velcro (TM) closure is sufficient to hold device 1 in a manner encompassing upper portion 5a of scrotum 5, but confining testicles 6 to lower portion 5b until these last are released by a gentle pull on a free or "tab" portion 4 adjacent end 4a of device 1, disengaging closure 2,3 and reopening annulus 1c. It may be noted here that when closed, device 1 is similar in shape to a sigma, the Greek symbol "$\sigma$" (or the mirror image of same, depending on the direction of winding—clockwise in FIG. 5—the term "sigma" being intended herein to cover both clockwise and counterclockwise winding).

In more detail, now, the material of band 1a should be suitably soft to avoid discomfort and should be either disposable or easily washable—e.g., a soft material such as velour, to which Velcro closure elements 2,3 are sewn, say, in a conventional mode of attachment. For the flat band embodiments of FIGS. 1-6, a suitable length "L"—inclusive of that of tab 4—has been found to be about $7\frac{1}{2}$ to $10\frac{1}{2}$ inches (19 to 27 cm) to accommodate the variation in individuals. As to the band's width "W," it preferably corresponds substantially to the distance "D" between the rest position of testicles 6 (see FIG. 4) and base 11a of male organ 11 adjacent juncture of the latter with the body 12. A width of about $\frac{5}{8}$ to $\frac{3}{4}$ inch (1.6 to 1.9 cm) has been found suitable for many males. Velcro closures 2,3 in those sizes are readily available commercially. Where scrotum 5 is short in length (5a+5b) to begin with, a band having an even narrower width W may be necessary, as discussed subsequently.

Considering, next, the length of the elements 2,3 of Velcro closures, the length L2 of hook-bearing member 2 should be at least $\frac{1}{2}$ inch (1.3 cm) for reliability of fastening, as is known, with lengths longer than the minimum being preferable. Length L3 of bed 3 should likewise be at least $\frac{1}{2}$ inch (1.3 cm) for proper attachment, but coverage of about half the length L–roughly 4 inches (10 cm)—is desirable (as shown in FIGS. 1-3) to allow advantageously a full range of adjustability to meet each individual's requirements. Either or both of the elements of Velcro closure 2,3 may actually extend over most of the length L of band 1a, but this results in potential discomfort in view of the prickliness of hook-bearing member 2, and is thus neither beneficial nor cost effective.

Clinical testing reveals that the male experiences no pain or discomfort when device 1 is used in the manner shown in FIGS. 4,5 to prevent testicles 6 from making their ascent as a preliminary to ejaculation. Other forms of fastening (e.g., adhesives, snap fasteners, etc.) are also usable and even a long, thick cord (not shown) made of a likewise suitably soft material and tied around scrotum 5 with a knot can give satisfactory results in many instances. It should be noted here that scrotum 5 varies from one man to another, however, not only in girth (as mentioned earlier), but also in length. A wide band 1a such as shown in FIG. 5 is preferred over such a cord because the interface 9 with scrotum 5 is larger and better defined, providing more positive control for a given size of opening 1b as it avoids a tendency for rolling displayed by the cord, a tendency found undesirable when scrotum 5 is longer than average. On the other hand, where scrotum 5 is short (length 5a+5b in FIG. 4) to begin with, a band 1a having a width W even less than that of the narrowest Velcro material available commercially may be required. Preferably, as shown in FIG. 6, a portion 14 of band 1a between opposing ends 15, 16 of elements 2, 3—respectively—has its edges cut back uniformly to yield a width reduced to about half that of the adjoining elements 2,3 (i.e., to 5/16 inch) so as to meet the requirement. Alternatively, the requirement may be met by slitting the narrow commercial Velcro material ($\frac{5}{8}$ inch) along its centerline. This alternative is not preferred because of potential problems in alignment of the narrowed elements 2,3 for proper engagement.

In operation, device 1 is placed around the upper portion 5a of scrotum 5 just above the testicles 6 in lower portion 5b well before onset of ejaculation, and preferably before the male is sexually aroused. To begin with, hook-bearing member 2 is placed in front of scrotum 5 adjacent to and immediately above testicles 6, with member 2 facing outward. Then, the end 4a of band 1a is brought around to encircle scrotum 5 just above testicles 6 as shown in FIG. 4 and pulled to form the ring-like or annular opening 1b of diameter roughly equal to that of one of the testicles 6 (as shown in FIGS. 4,5) before pressing bed 3 against hook-bearing member 2 to lock closure 2,3 together. At least a half-inch bare part of band 1a is always provided as a tab section 4 between bed portion 3 and end 4a so that it always hangs free and is readily graspable, being external to annulus 1c. Thereafter, when tab 4 is grasped between the thumb and a finger of either partner at a desired time, a simple tug on the tab releases band 1a to allow its complete removal—as is usually preferred to avoid discomfort resulting from presence of prickly hooks of disengaged element 2. The released and removed band 1a then no longer restrains ascent of testicles 6 such that ejaculation occurs only after the desired delay. Only prolonged sexual activity or release of device 1 will permit ejaculation to take place.

Device 1 has many uses, one of which is prolongation of sexual pleasure. Medically, device 1 is useful for treatment of premature ejaculation and treatment of certain cases of female frigidity, particularly those resulting from the female's fear that she cannot allow herself to become excited because her partner will be unable to delay ejaculation long enough to permit her to achieve satisfaction. Device 1 thus has value in promoting marital harmony, as readily seen.

In summary, the foregoing has described a method and device for control of the timing of male ejaculation by use of an annulusforming band 1a of width "W" approximating the distance between base 11a of male organ 11 and testicles 6, the annulus 1c formed being closed by adjustably connecting interengageable elements 2,3 (velcro TM strips or equivalent coatings with a suitable adhesive) around upper portion 5a of scrotum 5 to confine testicles 6 to lower portion 5b of scrotum 5, thus delaying ejaculation until annulus 1c is opened by a pull on tab 4 at free end 4a of band 1a.

Having described the method and device as above it will be clear to those skilled in the art that many changes could be made without departing from the spirit and scope of the invention. For example, dimensions could be changed to fit individuals having body proportions beyond the high end of the normal range, stronger or softer band materials could be substituted, the corners of free end 4a could be rounded, etc.

I claim:

1. A method for delaying ejaculation by a male organ, the organ having a base with a scrotum depending therefrom, the scrotum having testicles located in a lower portion thereof, the testicles normally being distal from said base by a particular distance; comprising the steps of:
    a) providing an openable and closable flexible annulus-forming member having a width substantially equal to said distance,
    b) prior to sexual activity which raises the testicles to a position proximate said base, placing said annulus-forming member solely circumscrotally while said member is open and entirely located between the base and the testicles within said lower portion of the scrotum,
    c) juxtaposing an end of said member and an intermediate portion thereof to form, solely circumscrotally below the base, an annulus of a size sufficiently small to confine the testicles to said lower portion of the scrotum, yet sufficiently large to avoid any clamping of the scrotum and its contents;
    d) closing said annulus by disengageable connection of said end and said intermediate portion of the member, said closing holding the testicles as confined,
    e) disengaging said connection to open the annulus when desired to free the testicles for ascent during sexual activity, thereby permitting a delayed ejaculation, and
    f) concomitantly removing said annulus-forming member in the entirely to a location remote from said scrotum.

2. The method of claim 1, wherein a tab-like section of said member at said other end is external to the annulus, and said steps of disengaging and removing occur in response to a pull on said tab-like section.

3. A method for delaying ejaculation by a male organ, the organ having a base with a scrotum depending therefrom, the scrotum having testicles located in a lower portion thereof, and the testicles normally being distal from the base by a particular distance; comprising the steps of:
    a) providing an openable and closable flexible annulus-forming member having an upper and lower lateral boundary defining a width substantially equal to said particular distance,
    b) prior to sexual activity which raises said testicles to a position proximate said base and while said member is open, placing said annulus-forming member solely circumscrotally with said upper lateral boundary lying solely below the base,
    c) forming a portion of said annulus-forming member less than the whole into an annulus, with the remainder lying extending of said annulus;
    d) sizing the annulus sufficiently small to confine the testicles to said lower portion of the scrotum, yet sufficiently large to avoid any clamping of the scrotum and its contents;
    e) closing said annulus subsequent to said forming and prior to engaging in said sexual activity, thereby holding the testicles as confined, and
    f) opening the annulus and removing the entire member from the vicinity of the scrotum by manual manipulation of said remainder when desired to free the testicles for ascent during the sexual activity, thereby permitting ejaculation.

4. A method for delaying ejaculation by the generative organ of a male, the organ having a base with a scrotum depending therefrom, the scrotum having a first portion proximal to the base and a second portion containing testicles normally resting at a particular distance from the base when the scrotum is in an inactive state, said testicles having a maximum combined cross-section of given area; comprising the steps of:
    a) providing a flexible sigma-shaped member having a single loop with a pair of spaced lateral boundaries defining a width for said sigma-shaped member corresponding to a substantial fraction of said particular distance, a tail-like projection externally of said loop, and a manually-operable, disruptible fastening for completing said loop;
    b) prior to sexual activity which raises said testicles to a position proximate said base, interfacing said loop with said first portion of the scrotum such that said pair of spaced lateral boundaries are located solely below said base;
    c) adjusting the circumference of said loop to encompass an area non-clamping with respect to said first portion of the scrotum but substantially less than said given area, thereby to confine said testicles to said second portion of the scrotum;
    d) pulling on said tail-like projection of the sigma-shaped member to disrupt said fastening to open the loop and concomitantly move the opened-loop, sigma-shaped member to a location remote from said scrotum, thus freeing said testicles from confinement to said second portion of the scrotum and eliminating contact with potentially annoying fastening elements on the opened loop, both without interruption of sexual activity.

5. A method as defined in claim 4, wherein said flexible, sigma-shaped member comprises a thin flat band, said band having a first and a second element thereon respectively positioned adjacent one end of said band and a point on the band intermediate said one end and said tail-like projection, the method including as further steps between steps c) and d), the juxtaposition and interengagement of at least a portion of said first and said second elements to permit formation and closure of said loop selectively at a plurality of longitudinal locations intermediate of the band, said locations being exclusive of the tail-like projection.

* * * * *